United States Patent [19]

Voigt et al.

[11] Patent Number: 5,403,885
[45] Date of Patent: Apr. 4, 1995

[54] TRANSPARENT MATERIAL FOR DENTAL APPLICATIONS

[75] Inventors: Reiner Voigt, Leverkusen; Hans-Herrmann Schulz, Cologne; Dieter Wrobel, Leverkusen, all of Germany

[73] Assignee: Bayer Aktiengesellschaft, Leverkusen, Germany

[21] Appl. No.: 156,660

[22] Filed: Nov. 22, 1993

Related U.S. Application Data

[63] Continuation of Ser. No. 905,258, Jun. 26, 1992, abandoned.

[30] Foreign Application Priority Data

Jul. 5, 1991 [DE] Germany ............. 41 22 310.1

[51] Int. Cl.⁶ ............................... C08K 3/36
[52] U.S. Cl. .................. 524/731; 524/862; 523/109; 523/120; 264/18; 264/19; 433/226; 433/228.1
[58] Field of Search ............... 524/731, 862; 523/109, 523/120

[56] References Cited

U.S. PATENT DOCUMENTS

| | | | |
|---|---|---|---|
| 3,699,073 | 10/1972 | Wada et al. | 524/787 |
| 4,013,611 | 3/1977 | Hechtl et al. | 524/862 |
| 4,035,453 | 7/1977 | Hittmair et al. | 264/16 |
| 4,101,499 | 7/1978 | Herzig | 524/731 |
| 4,965,295 | 10/1990 | Schwabe et al. | 523/109 |
| 5,086,147 | 2/1992 | Ikeno et al. | 528/15 |

FOREIGN PATENT DOCUMENTS 2535334 8/1975 Germany.
2646726 10/1976 Germany.

OTHER PUBLICATIONS

R. G. Graig, Restaurative Dental Materials, The C. V. Moosbe-Comp., St. Louis, 1980.
W. Noll, Chemistry and Tech of Silicones, p. 3.

Primary Examiner—Melvyn I. Marquis
Assistant Examiner—Margaret W. Glass
Attorney, Agent, or Firm—Sprung Horn Kramer & Woods

[57] ABSTRACT

The present invention relates to a transparent material based on addition-crosslinking polysiloxanes, which is used as occlusal print for molding side teeth composites.

5 Claims, No Drawings

TRANSPARENT MATERIAL FOR DENTAL APPLICATIONS

This application is a continuation of application Ser. No. 07/905,258, filed Jun. 26, 1992, now abandoned entitled TRANSPARENT MATERIAL FOR DENTAL, APPLICATIONS.

The present invention relates to a transparent material based on addition-crosslinking polysiloxanes, which is used as occlusal print for molding side teeth composites, as fixation rigid guide for brackets in orthodontics and preferably used in the dental field for bite registration. In addition, the use of transparent materials which make it possible to check adjustments or positions due to the transparency and achieve fixation by means of this material, for example by photopolymerisation, is in many cases desirable in dental applications.

The bite-registering materials in dentistry mentioned as preferred are used in order to fix the correct relative position of lower jaw to upper jaw in the mouth and to transfer this position to the models in the dental laboratory. For this purpose, waxes and, preferably, elastomeric materials, such as polyethers and silicones are used. Bite-registering materials have to fulfil particular requirements. They must have stable consistency and be distinguished by a high final hardness, low elastic deformability and a minimum dimensional change. The material according to the invention based on addition-crosslinking silicone compositions is distinguished by high transparency, which makes it possible to check the dental position in the mouth of the patient and, if necessary, to correct the biting position under visual control. Moreover, the processing time of the material can be set to a very small value. A processing time of only about 35–45 seconds reduces the risk of a positional shift of the lower jaw from the position first adopted by the patient. It is, for example, possible to remove the squeeze bite from the mouth after 2 minutes 30 seconds, measured from the beginning of mixing. After setting is complete, i.e. after removal from the mouth, this addition-crosslinking silicone material does not undergo any clinically relevant dimensional changes and thus results in registered bites which are permanently stable on storage. It is also of particular importance that the model position in the registered bite can be checked owing to the transparency. Shifts in the positions of the models, which may require a time-consuming correction of the finished work in the mouth, can be discovered even before production of the dentures, due to this possibility of a check, which is not possible with all other non-transparent materials.

Dental impression materials based on addition-crosslinking polysiloxanes are known per se (see, for example, R. G. Graig, Restaurative Dental Materials, The C. V. Moosbe-Comp., St. Louis, 1980, p. 195 et seq.).

In general, these compositions comprise a base paste containing a silicone oil, filler and crosslinking agent and a catalyst paste consisting of silicone oil, filler and catalyst.

Upon application, the base and catalyst paste are mixed in a weight or volume ratio of preferably 1:1 and applied to the jaw portion to be modelled by means of a syringe and/or modelling spoon. After crosslinking by a polyaddition reaction, the rubber-like model is removed from the mouth of the patient and then cast together with an aqueous slurry of modelling gypsum.

Bite-registering materials based on addition-crosslinking silicones are also known and commercially available. They have a similar composition to the abovementioned dental impression materials. The higher final hardnesses and lower elastic deformations are achieved by the use of even larger portions of fillers. The short processing times of these compositions can be achieved by a higher platinum catalyst content. These two-component materials of high filler content are non-transparent and produce a hard and brittle rubber after the addition reaction.

From U.S. Pat. No. 4,571,188 an occlusal matrix for light cured composites is known. This matrix is based on 6% polymethylhydro(65–70%)-dimethylsiloxane copolymer and 94% vinyldimethyl terminated polydimethylsiloxane (viscosity 60,000 csk) and as a catalyst 1% chloroplatinic acid complex and 99% vinyldimethyl terminated polydimethylsiloxane (viscosity 60,000 csk) is used. The specification of this patent is teaching to mix base and catalyst together with a spatula, to place the material obtained on the occlusal surfaces of a tooth to be restored and the surrounding dental structure with said spatula and to allow the mixture to set. Thereafter, the negative reproduction obtained should be removed, the tooth is to be restored with a light curing composite and the occlusal matrix is placed again to the area thereafter. Then the composite is cured with light. However, as the included comparison examples clearly show the material is lacking sufficient applicability and mechanical strength.

The use according to the invention of compounds of highly disperse, active fillers in silicone oils, which are described in DE-A-2,535,334, and the use according to the invention of a short-chain polysiloxane compound rich in vinyl groups and, if appropriate, of a short-chain QM resin containing vinyl groups give highly viscous, transparent pastes, which crosslink within a very short period of time to give hard rubbers having good tear strength and high transparency.

These QM resins are characterised in that, as explained in W. Noll, Chemie und Technologie der Silikone (Chemistry and Technology of Silicones), Verlag Chemie, Weinheim, 2nd edition, 1964, page 3, they contain tetrafunctional $SiO_{4/2}$ as Q units and monofunctional $R_3SiO_{1/2}$ as M building blocks, in which R can be vinyl, methyl, ethyl or phenyl. Moreover, trifunctional $RSiO_{3/2}$ can be present as T units and bifunctional $R_2SiO_{2/2}$ as D units, where R has the same meaning as defined above. The content according to the invention of 0–10% by weight of QM resin, preferably 0–5% by weight of QM resin in the entire silicone system achieves a significant improvement in the crosslinking density and thus a higher tear strength and hardness of the elastomeric product.

Accordingly, the invention relates to compositions curable at ambient temperature and based on polysiloxane, which compositions crosslink by the addition process, comprising a) organopolysiloxanes having two or more vinyl groups in the molecule, b) organohydrogenpolysiloxanes having two or more Si-H groups in the molecule, c) a catalyst for accelerating the addition reaction and, if desired, d) dyestuffs, characterised in that the compositions additionally comprise e) compounds of highly disperse, active fillers in a silicone oil,
f) short-chain organopolysiloxanes having two or more vinyl groups in the molecule and
g) if desired, a low-molecular-weight QM resin containing vinyl and ethoxy groups and being homogeneously soluble in a), which resin first has a vinyl group content of 0.5–8 mmol/g and secondly comprises $SiO_{4/2}$, $RO_{\frac{1}{2}}$ and $R_3SiO_{\frac{1}{2}}$ units, where R represents a methyl, vinyl, phenyl or ethyl group, and has an ethoxy group content of less than 4 mmol/g.

Component b) of the abovementioned recipe is present in the base paste and component c) in the catalyst paste. Base and catalyst paste of the bite-registering material according to the invention are distinguished by high transparency and long shelf life with respect to viscosity; the registered bites prepared therefrom have hardness, high transparency and tear strength in combination with low elastic deformation.

The organopolysiloxanes a) are preferably silicone oils composed of polydimethylsiloxanes known per se, terminated at the vinyl end and having a viscosity in the range from 100 to 100,000 mPa.s, preferably 200 to 10,000 mPa.s at 20° C.

The organohydrogenpolysiloxanes b) used as crosslinking agent are likewise polydimethylsiloxanes known per se, which have hydrogen atoms on at least two silicone atoms in its molecule.

Catalyst c) is a platinum complex prepared from hexachloroplatinic acid. These compounds are also known per se.

Dyestuffs d), which, if desired, are used for distinguishing between base and catalyst paste and for control of the mixing, should be finely dispersed so as not to interfere in the transparency. Not only inorganic colour pigments organic ones are preferred. In accordance with DE-A-3,544,619, solutions of dyestuffs in isoparaffins, such as 2,2,4,4,6,6,8-heptamethylnonane ($C_{16}H_{34}$) or 2,2,4,4,6,6,8,8,10-nonamethylundecane ($C_{20}H_{42}$) can be used particularly preferably.

Compounds e) to be used according to the invention are, e.g., as described in DE-A-2,535,334, prepared from silica prepared by precipitation or pyrogenically having a specific surface area of more than 50 m$^2$/g according to BET and a polydimethylsiloxane terminated at the trimethylsilane and/or vinyl end and having a viscosity of preferably between 100 and 200,000 mPa.s at 20° C. with the use of modifying auxiliaries, for example hexamethyldisilazane or tetramethyldivinyldisilazane.

This is done by treating the filler during the incorporation process in the presence of water with modifying agents of the general formula

$(R_3Si)_n-X$ in which R represents a substituted or unsubstituted, saturated or aliphatically unsaturated hydrocarbon radical having up to 10 C atoms, X denotes halogen, H OH, OR, S, OOCR, N or NY (Y is hydrogen or R) and n is 1, 2 or 3.

The compounds suitable for the compositions according to the invention contain the following individual components:
1. 20 to 1000, preferably 50–200, parts by weight of a linear polyorganosiloxane of the general formula

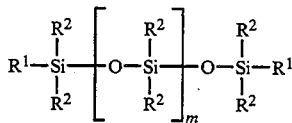

in which $R^2$ represents identical or different, monovalent, substituted or unsubstituted hydrocarbon radicals, $R^1$ has the same meaning as $R^2$ and moreover can represent a vinyl radical and m is a positive integer;

2. 5 to 500, preferably 10–100, parts by weight of a highly disperse, active filler having a BET surface area of at least 50 m$^2$/g.

The abovementioned component 1) is a linear polyorganosiloxane whose molecular chain has been saturated with monovalent hydrocarbon radicals $R^2$. $R^2$ can be a substituted or unsubstituted hydrocarbon radical and is preferably selected from alkyl radicals, such as, for example, methyl, ethyl, propyl, butyl, hexyl, i-propyl, amyl, or aryl radicals, such as, for example, tolyl, xylyl, ethylphenyl, or aralkyl radicals, such as, for example, benzyl, phenylethyl or halogen-substituted alkyl or aryl radicals, such as, for example, chloromethyl, 3,3,3-trifluoropropyl, chlorophenyl, tetrachlorophenyl, difluorophenyl and alkenyl radicals, such as, for example, vinyl, allyl. In addition, $R^2$ also represents cyanoalkyl, cycloalkyl and cycloalkenyl radicals.

$R^1$ has the same meaning as $R^2$, but moreover can also be a vinyl group.

In a molecule of component 1), different radicals $R^1$ and $R^2$ can be present.

The magnitude of the number m determines the viscosity of the linear polyorganosiloxane and is selected such that the viscosity of the linear polyorganosiloxane is preferably between 100 mPa.s and 2×10$^5$ mPa.s at 20° C. Component 1) can also be composed of mixtures of polymers having a different value for m.

Component 2) is a commercially available, highly disperse, active filler having a BET surface area of at least 50 m$^2$/g. Substances such as $TiO_2$, $Al_2O_3$, ZnO or, preferably, pyrogenically obtained or wet-precipitated silica are suitable. The preparation process and the chemical nature of the filler are irrelevant to the use according to the invention. The only important feature is that it is a filler having a BET surface area in the order of magnitude given. Furthermore, it is advantageous if no filler is used which was modified during or after preparation. Examples of suitable fillers which may be mentioned are pyrogenically obtained or wet-precipitated silica which are available under the tradenames AEROSIL ® (Degussa), CABOSIL ® (Cabot), HDK ® (Wacker Chemie), pyrogenically obtained alumina or titanium dioxide under the name ALUMINIUMOXID O ® or TITANDIOXID P 25 ® (Degussa) or ZINKOXID AKTIV ® (BAYER AG).

Incorporation of the highly disperse, active filler is carried out according to DE-A-2,535,334 such that the filler is modified during the incorporation process in the presence of component 1) in a suitable form at the surface. This makes it necessary that before addition of the filler the modifying agent is added to component 1). The modifying agent is a substance capable of modifying the surface of the filler in the desired manner without the presence of an additional catalyst but does not undergo a chemical reaction with component 1) under the reaction conditions chosen. It has been found that compounds of the general formula $$(R_3Si)_nX$$

are suitable for modifying fillers in the desired manner in the presence of component 1). In this formula, R has the abovementioned meaning, n is a positive number and can have the value 1, 2 or 3 and X is a radical of the formula H, OH, OR, halogen, S, OOCR, N or NY (in which R has the meaning given in a) and Y is a monovalent hydrocarbon radical or hydrogen). Examples which may be mentioned are: hexamethyldisilazane, trimethylsilane, trimethylchlorosilane, trimethylethoxysilane, triorganosilyl acylates or triorganosilylamines.

According to the invention, compounds in which the radical R is a methyl radical and the radical X represents the group NY, where Y is preferably a hydrogen atom, are particularly preferred.

As a rule, the modifying agent is added in an amount of 1–50, preferably 3–20, parts by weight.

It is preferred to add water in an amount of 0.1 to 10 parts by weight, preferably 2 to 6 parts by weight, to the mixture of component 1) and the modifying agent before adding the highly disperse, active filler. The presence of water favours the reaction between the modifying agent and the highly disperse filler. In addition, the water promotes an accelerated, uniform distribution of the filler in the presence of the modifying agent.

Incorporation of the highly disperse, active filler takes place at room temperature or only slightly elevated temperature. The time of incorporation is not critical, and no particular precautionary measures have to be taken. It is advantageous to add the highly disperse, active filler to the mixture of component 1), modifying agent and water not all at once but in portions, so that the amount of highly disperse, active filler added each time is wetted and incorporated within a short period. Distribution of the highly disperse, active filler in the mixture of component 1), modifying agent and water can be carried out by means of commercially available apparatuses suitable for this, preferably by means of so-called Z kneaders or planetary stirrers.

The amount of highly disperse, active filler to be incorporated depends on the desired consistency of the mixture and, in the case of mixtures in which component 1) contains radicals $R^1$ or $R^2$ which can undergo a crosslinking reaction at room temperature in the presence of suitable crosslinking substances, on the required mechanical properties of the crosslinked rubber.

After complete incorporation of the highly disperse, active filler, the mixture comprising component 1), modifying agent, water and filler is preferably subjected to a mechanical stress of short duration (for example superatmospheric pressure, compression between rolls, kneading stress) such that the mixture remains in the tightly sealed mixing apparatus for 10 minutes to 2 hours. After exposure of the mixture to mechanical stress is complete, excess modifying agent and water are removed either by applying a vacuum or by opening and ventilating the mixing apparatus at elevated temperature until excess modifying agent and water have been volatilised virtually completely. Preferably, the temperature is increased and a vacuum is applied at the same time.

The short-chain polydimethylsiloxanes f) terminated at the vinyl end and used according to the invention are known per se. Thus, in DE-A-2,646,726, compounds of the general formula $$CH_2=CH-R_2SiO-(SiR_2O)_n-SiR_2-CH=CH_2$$

in which R denotes identical or different, monovalent, substituted or unsubstituted hydrocarbon radicals free from aliphatic multiple bonds and n denotes 0 or an integer having a value from 1 to 6 are described. These compounds are used in amounts of 1 to 5000 ppm by weight, relative to the total weight of all substances used, as inhibitors for controlling the crosslinking rate of addition-crosslinking silicone impression materials.

Surprisingly, it has now been found that compounds of the same abovementioned general formula, in which R has the same abovementioned meaning but n is an integer from 10 to 20, do not at all act as an inhibitor and can be used in an amount from 1 to 8 per cent by weight, relative to the total amount, while maintaining short reaction times of the mixture. The crosslinking rubbers have higher hardness.

QM resins g) used, if desired, according to the invention are known per se. Their preparation is described, for example, in U.S. Pat. Nos. 2,676,182, 2,857,356 and 3,527,659.

The essential features of the use according to the invention are
  that the QM resins have such a low molecular weight that they produce a transparent solution in the polydimethylsiloxanes terminated at the vinyl end and their mixtures lead to transparent final products. As a rule, QM resins of this type have a viscosity from 150 to 1500 mPa.s at 20° C.;
  that the SiOH content of the QM resins is sufficiently low so as not to lead to optical interferences due to bubbles of liberated hydrogen gas;
  that the content of volatile and/or unreactive molecules is sufficiently low so as not to reduce the dimensional stability of the moulded article; and
  that the QM resins have a vinyl content of 0.5 to 8 mmol/g and an ethoxy content of 0.2 to 3 mmol/g.

The ratio of the sum of $R_3SiO_{\frac{1}{2}}$ and $EtO_{\frac{1}{2}}$ units to $SiO_{4/2}$ units should be less than 2.5 and its lower limit is determined by the transparent solubility of the QM resins in the polydimethylsiloxanes terminated at the vinyl end or by the transparency of the final products.

Moreover, the QM resins can contain small amounts of $R_2SiO$ and $RSiO_{3/2}$ units without interfering in the use according to the invention, although the sum of $R_2SiO$ and $RSiO_{3/2}$ units should not exceed 20 mol % by weight.

A preferred QM resin has the formula $$[SiO_{4/2}][(CH_3)_2CH_2=CHSiO_{\frac{1}{2}}]_{0.9-1.4}[C_2H_5O_{\frac{1}{2}}]_{0.4-0.5}$$

has of vinyl content of 5.5–6.5 mmol/g and a viscosity of 500–800 mPa.s at 23° C.

Preferably, bite-registering materials according to the invention (i.e. the mixture of base and catalyst paste) have the following relative amounts (in % by weight, relative to the entire paste) of the individual components:

a) 5 to 30% by weight, in particular 10–25% by weight, of the polysiloxane containing vinyl groups
b) 1–10% by weight, in particular 2–6% by weight, of crosslinking agent c) 0.005–2% by weight, in particular 0.01 to 1% by weight, of catalyst
d) 0–1% by weight, in particular 0 to 0.5% by weight, of dyestuffs
e) 30–80% by weight, in particular 50–75% by weight, of the compounds described hereinabove
f) 1–10% by weight, in particular 2–6% by weight, of the short-chain polysiloxane according to the invention containing vinyl groups and
g) 0–10% by weight, in particular 0–5% by weight, of the short-chain QM resin according to the invention containing vinyl groups.

Preferably, the compounds to be used according to the invention contain 5–50% by weight (relative to the entire compound), in particular 15–40% by weight, of highly disperse, active fillers.

The examples which follow, in which all parts are by weight, illustrate the invention.

EXAMPLE 1

In a kneader, 270 parts of polydimethylsiloxane terminated at the vinyl end and having a viscosity of 10 Pa.s and 310 parts of polydimethylsiloxane terminated at the vinyl end and having a viscosity of 65 Pa.s at 20° C. are mixed with 68 parts of hexamethyldisilazane and 12 parts of tetramethyldivinyldisilazane and 50 parts of water, and the mixture is then mixed with 330 parts of pyrogenic silica having a BET surface area of 300 m²/g to give a homogeneous composition. The mixture was first heated to 130° C. and stirred in a sealed kneader for 1.5 hours and then freed from highly volatile components at 160° C. under vacuum for 1 hour. After cooling, the compound is diluted with 120 parts of polydimethylsiloxane terminated at the vinyl end and having a viscosity of 10 Pa.s at 20° C. with stirring.

EXAMPLE 2

The base paste of a bite-registering material was prepared in a kneader by mixing 70.0 parts of the compound from Example 1, 6.6 parts of a polydimethylsiloxane containing SiH groups and having an SiH content of 7.5 mmol/g and a viscosity of 60 mPa.s at 20° C. and 23.4 parts of a polydimethylsiloxane terminated at the vinyl end and having a viscosity of 200 mPa.s at 20° C.

The corresponding catalyst paste was obtained by mixing 69.2 parts of the compound from Example 1, 0.8 part of a complex of platinum and divinyltetramethyldisiloxane as catalyst, 10 parts of the short-chain polydimethylsiloxane terminated at the vinyl end and having an SiVi content of 1.8 mmol/g and a viscosity of 10 mPa.s at 20° C. and 20 parts of a polydimethylsiloxane terminated at the vinyl end and having a viscosity of 200 mPa.s at 20° C.

Both pastes have a viscosity of about 50,000 mPa.s at 20° C. and were transparent. They were each poured into a chamber of a double cartridge and pressed through a fitted static mixer by means of a double-piston gun and mixed therewith. 30 seconds after leaving the static mixer, the processing time had elapsed, due to an increase in viscosity caused by the addition reaction which was beginning, and after a further 2 minutes, the mixture had been crosslinked to give a transparent rubber having good tear strength and a Shore A hardness of 69. This bite-registering material was evaluated as good in the practical application test.

EXAMPLE 3

Preparation of a bite-registering material base paste was carried out in a kneader by mixing 67.5 parts of the compound from Example 1, 24.0 parts of a polydimethylsiloxane containing SiH groups and having an SiH content of 7.5 mmol/g and a viscosity of 60 mPa.s at 20° C. and 8.5 parts of a polydimethylsiloxane terminated at the vinyl end and having a viscosity of 200 mPa.s at 20° C.

The corresponding catalyst paste was prepared in the same manner by mixing 70.0 parts of the compound from Example 1, 15.2 parts of a polydimethylsiloxane terminated at the vinyl end and having a viscosity of 200 mPa.s at 20° C., 9.0 parts of a short-chain polydimethylsiloxane terminated at the vinyl end and having an SiVi content of 1.8 mmol/g and a viscosity of 10 mPa.s at 20° C., 5.0 parts of a QM resin of the formula $$[SiO_{4/2}][MeViSiO_{\frac{1}{2}}]_{1.0}[EtO_{\frac{1}{2}}]_{0.4}$$

having a viscosity of 800 mPa.s at 20° C. and 0.8 part of a complex of platinum and divinyltetramethyldisiloxane as the catalyst.

The viscosity of the base paste was about 47,000 mPa.s and that of the catalyst paste about 52,000 mPa.s at 20° C. Both pastes were transparent. The pastes mixed as described above had a processing time of 45 seconds and a setting time of 2 minutes 45 seconds. The crosslinked rubber was transparent, had high tear strength and a Shore A hardness of 78. Evaluation of this bite-registering material in practical application was very good.

EXAMPLE 4

(Comparison)
In a kneader, the base paste of a bite-registering material was prepared by mixing 70.0 parts of the compound from Example 1, 5.8 parts of a polydimethylsiloxane containing SiH groups and having an SiH content of 7.5 mmol/g and a viscosity of 60 mPa.s at 20° C. and 24.2 parts of a polydimethylsiloxane terminated at the vinyl end and having a viscosity of 200 mPa.s at 20° C.

The preparation of the corresponding catalyst paste was carried out in a kneader by mixing 76.4 parts of the compound from Example 1, 0.6 part of a complex of platinum and divinyltetramethyldisiloxane as the catalyst and 24.0 parts of a polydimethylsiloxane terminated at the vinyl end and having a viscosity of 200 mPa.s at 20° C.

The base paste had a viscosity of about 48,000 mPa.s and the catalyst paste had a viscosity of about 58,000 mPa.s at 20° C. Both pastes were transparent. The pastes were poured into a double cartridge and pressed through the fitted static mixer by means of a double-piston gun and gave a processing time of 40 seconds and a setting time of 2 minutes 30 seconds. The crosslinked rubber had very good transparency and tear strength but had a Shore A hardness of only 50 and was very flexible. The practical application test evaluated the material as not very suitable due to its low hardness and high flexibility.

EXAMPLE 5

(Comparison)
The base paste of a bite-registering material was prepared in a kneader by mixing 10.0 parts of the compound from Example 1, 5.8 parts of a polydimethylsiloxane containing SiH groups and having an SiH content of 7.5 mmol/g and a viscosity of 60 mPa.s at 20° C., 24.0 parts of a polydimethylsiloxane terminated at the vinyl end and having a viscosity of 1,000 mPa.s at 20° C., 59.8 parts of very fine cristobalite powder having an average particle size of about 4 μm and 0.4 part of an organic coloured pigment.

The corresponding catalyst paste was obtained by mixing 16.5 parts of the compound from Example 1, 23.0 parts of a polydimethylsiloxane terminated at the vinyl end and having a viscosity of 1,000 mPa.s at 20° C., 0.5 part of a complex of platinum and divinyltetramethyldisiloxane and 60.0 parts of the abovementioned very fine cristobalite powder.

The base paste had a viscosity of about 54,000 mPa.s and the catalyst paste had a viscosity of about 60,000 mPa.s at 20° C. Both pastes were opaque. The pastes mixed as described above had a processing time of 45 seconds and a setting time of 2 minutes 45 seconds. The crosslinked rubber had low tear strength, a Shore A hardness of 77 and was not transparent. This bite-registering material was evaluated in the practical application test as moderately suitable due to its non-transparency and slight brittleness.

EXAMPLE 6

(According to U.S. Pat. No. 4,571,188)

A base paste is prepared by mixing 94% by weight vinyl terminated polydimethylsiloxane (65,000 mPa.s) and 6% by weight crosslinker (70% by weight dimethyl-, 30% by weight methylhydrogensiloxane). A catalyst paste is made from 99,8% by weight vinyldimethyl terminated polydimethylsiloxane (65,000 mPa.s) and 0,2% by weight platinum catalyst.

The mixture has a processing time of 20 seconds and a setting time of 1 minute. However, the crosslinked product was not transparent because of numerous air bubbles in the material

EXAMPLE 7

In order to avoid the negative results in clearness of the material obtained from example 6, the components were poured into a double cartridge and pressed through the fitted static mixer by means of a double-piston gun. The processing time was 22 seconds, the setting time 1 minute. The Shore A hardness was only 18, the product was of good transparency but very low tear strength.

EXAMPLE 8

Example 7 was modified by forming the base paste of 96% by weight of the vinyl terminated polydimethylsiloxane and 4% by weight of crosslinker as described in Example 6. The catalyst paste was the same.

The processing time was 30 seconds, the setting time 1 minute 20 seconds, the Shore A hardness was 19, the product was of good transparency but very low tear strength.

EXAMPLE 9

The above mixture was again modified by forming a base paste from 94% by weight of the same vinyldimethyl terminated polydimethylsiloxane and 6% by weight of crosslinker (90% by weight dimethyl- and 10% by weight methylhydrogensiloxane). The catalyst paste was prepared from 97% by weight vinyldimethyl terminated polydimethylsiloxane as described above and 3% by weight of platinum catalyst. The processing time was 2 minutes and 30 seconds, the setting time about 6 minutes. The Shore A hardness was 18, the product was of good transparency but of a low tear strength.

The viscosity of the mixture before setting is too low for dental applicances since it would flow down from the teeth into the patients jaw.

EXAMPLE 10

According to the present invention Example 3 described above was modified by employing a catalyst component comprising 2,5% by weight of the QM-resin instead of 5% by weight. The processing time was 45 seconds, the setting time 3 minutes. The Shore A hardness was 73, the product is almost transparent and of a high tear strength.

The above examples clearly show the superiority of composiions according to the present invention. Those of the prior art exhibit not enough tear strength so they can hardly be removed from the patients teeth without being damaged. Because of the low hardness prior art compositions do not allow to form the surface of a composite used for filling cavities by means of an occlusal stamp,

We claim:

1. A transparent fast-curing polysiloxane addition-crosslinking composition comprising
   a) 5 to 30% by weight of a linear organopolysiloxane having at least to vinyl groups and a viscosity between 100 and 100,000 mPa.s at 20° C.;
   b) 1 to 10% by weight of an organohydrogenpolysiloxane crosslinking agent;
   c) 0.005 to 2% by weight of a catalyst for accelerating addition reaction;
   d) optionally a dyestuff;
   e) 30 to 80% by weight of a mixture of a polydimethylsiloxane terminated at each end by a vinyl radical and having a viscosity of between 100 and 200,000 mPa.s at 20° C. and silica prepared by precipitation or pyrogenically having a specific surface area of more than 50 m$^2$/g according to BET, the silica comprising 5 to 50% by weight of (e), the mixture having been prepared in the presence of water and hexamethyldisilazane as a modifying agent;
   f) 1 to 10% by weight of a short-chain organopolysiloxane of the formula $$CH_2=CH-R_2SiO-(SiR_2O)_nSiR_2-CH=CH_2$$

in which R denotes identical or different monovalent, substituted or unsubstituted hydrocarbon radicals free from aliphatic multiple bonds, and n denotes an integer having a value from 10 to 20; and
   g) optionally up to 10% by weight of a low-molecular-weight QM resin containing vinyl and ethoxy groups and being homogeneously soluble in a), which resin has a vinyl group content of 0.5–8 mmol/g and comprises $SiO_{4/2}$, $RO_{\frac{1}{2}}$  and $R_3SiO_{\frac{1}{2}}$ units, in which R represents a methyl, vinyl, phenyl or ethyl group, and has an ethoxy group content of less than 4 mmol/g.

2. A composition according to claim 1, wherein (f) is present in from 2 to 6% by weight, and (g) is present in from 0 to 5% by weight.

3. In a method for bite registration in dentistry the improvement consisting of applying the compositions according to claim 1.

4. In a method for molding side teeth composites the improvement consisting of applying the compositions according to claim 1 as occlusal stamp material.

5. In a method for preparing brackets in orthodontics the improvement consisting of applying the compositions according to claim 1 as a fixation rigid guide.

* * * * *

UNITED STATES PATENT AND TRADEMARK OFFICE
CERTIFICATE OF CORRECTION

PATENT NO.   : 5,403,885
DATED        : April 4, 1995
INVENTOR(S)  : Vo8gt, et al.

It is certified that error appears in the above-indentified patent and that said Letters Patent is hereby corrected as shown below:

Col. 10, claim 1   Delete " to " and substitute -- two --
line 4

Signed and Sealed this

Eighteenth Day of July, 1995

Attest:

BRUCE LEHMAN

*Attesting Officer*               *Commissioner of Patents and Trademarks*